US007049146B2

(12) United States Patent
Miller

(10) Patent No.: US 7,049,146 B2
(45) Date of Patent: *May 23, 2006

(54) CALIBRATION STANDARDS, METHODS, AND KITS FOR WATER DETERMINATION

(75) Inventor: Scott Andrew Miller, Beech Grove, IN (US)

(73) Assignee: Facet Analytical Services and Technology, LLC, Beech Grove, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/793,722

(22) Filed: Mar. 5, 2004

(65) Prior Publication Data

US 2004/0171161 A1    Sep. 2, 2004

Related U.S. Application Data

(63) Continuation-in-part of application No. 10/399,117, filed as application No. PCT/US01/27790 on Nov. 1, 2001.

(60) Provisional application No. 60/248,487, filed on Nov. 14, 2000.

(51) Int. Cl.
G01N 33/18    (2006.01)

(52) U.S. Cl. .............................. 436/42; 436/39; 436/8; 436/19

(58) Field of Classification Search .................. 422/61; 436/39, 42, 8, 19
See application file for complete search history.

(56) References Cited

U.S. PATENT DOCUMENTS

| 4,035,359 A | 7/1977 | Christensen et al. |
| 4,071,529 A | 1/1978 | Christensen et al. |
| 4,104,190 A | 8/1978 | Hartshorn |
| 4,143,129 A * | 3/1979 | Marsden ..................... 514/209 |
| 4,154,845 A | 5/1979 | Christensen et al. |
| 4,219,435 A | 8/1980 | Biard et al. |
| 4,631,305 A | 12/1986 | Guyer et al. |
| 4,684,650 A | 8/1987 | Bogeso |
| 4,818,325 A | 4/1989 | Hiraiwa et al. |
| 4,933,453 A | 6/1990 | Hrib et al. |
| 5,037,984 A | 8/1991 | Hrib et al. |
| 5,136,037 A | 8/1992 | Hrib et al. |
| 5,229,388 A | 7/1993 | Hrib et al. |
| 5,288,507 A * | 2/1994 | Sims et al. .................. 424/682 |
| 5,292,364 A | 3/1994 | Hiraiwa et al. |
| 5,340,541 A * | 8/1994 | Jackson et al. ............... 422/75 |
| 5,371,087 A | 12/1994 | Hrib et al. |
| 5,401,744 A | 3/1995 | Behme |
| 5,476,874 A | 12/1995 | Hungate et al. |
| 5,567,910 A | 10/1996 | Chattopadhyay |
| 5,612,217 A | 3/1997 | Shafiee et al. |
| 5,616,344 A | 4/1997 | Battist et al. |
| 5,646,148 A | 7/1997 | Huff et al. |
| 5,654,003 A | 8/1997 | Fuisz et al. |
| 5,674,854 A | 10/1997 | Bodley et al. |
| 5,747,540 A | 5/1998 | Coburn et al. |
| 5,801,186 A | 9/1998 | Hrib et al. |
| 5,807,841 A | 9/1998 | Huff et al. |
| 5,817,609 A | 10/1998 | He et al. |
| 5,830,500 A | 11/1998 | El-Rashidy et al. |
| 5,854,226 A | 12/1998 | Penkler et al. |
| 5,994,281 A | 11/1999 | He et al. |
| 6,010,719 A | 1/2000 | Remon et al. |
| 6,071,916 A | 6/2000 | Askin et al. |
| 6,074,998 A | 6/2000 | He et al. |
| 6,131,442 A * | 10/2000 | Krause .......................... 73/73 |
| 6,180,634 B1 | 1/2001 | Vacca et al. |
| 6,245,917 B1 | 6/2001 | Bosch et al. |
| 6,284,775 B1 | 9/2001 | Hrib et al. |
| 6,432,952 B1 | 8/2002 | Crocker et al. |
| 6,503,927 B1 | 1/2003 | Ronsen et al. |
| 6,509,347 B1 | 1/2003 | Xu et al. |
| 6,620,791 B1 | 9/2003 | Cooper et al. |
| 6,642,237 B1 | 11/2003 | Tata et al. |
| 6,667,299 B1 | 12/2003 | Ahlem et al. |
| 2002/0056206 A1 | 5/2002 | Pace et al. |
| 2002/0058065 A1 | 5/2002 | Guivarc'h et al. |
| 2002/0182723 A1 | 12/2002 | Zhang et al. |
| 2002/0188001 A1 | 12/2002 | Xu et al. |
| 2003/0060425 A1 | 3/2003 | Ahlem et al. |
| 2003/0083231 A1 | 5/2003 | Ahlem et al. |
| 2003/0125336 A1 | 7/2003 | Fleitz et al. |
| 2003/0166702 A1 | 9/2003 | Kor et al. |

FOREIGN PATENT DOCUMENTS

| EP | 0 482 465 A | 4/1992 |
| JP | 04297869 A2 | 10/1992 |
| WO | WO 02/40991 A2 | 5/2002 |

OTHER PUBLICATIONS

Gessneer G. Hawley, The Condensed Chemical Dictionary, 1981, p. 953, Tenth Edition, Van Nostrand Reinhold Company, U.S.A.

Neuss J D et al: Sodium Tartrate Dihydrate as a Primary Standard for Karl Fischer Reagent: Analytical Chemistry, American Chemical Society, Columbus, US, vol. 23, 1951, pp. 1332-1333, XP001042005 ISSN: 0003-2700 the whole document.

Ohm A: "Interaction of Bay t 3839 coprecipitates with insoluble excipients" European Journal of Pharmaceutics and Biopharmaceutics, Elsevier Science Publishers B.V., Amsterdam, NL, vol. 49, No. 2, Mar. 1, 2000, pp. 183-189, XP004257154 ISSN: 0939-6411 p. 186, left-hand column—p. 188, Left-hand column.

(Continued)

Primary Examiner—Maureen M. Wallenhorst
(74) Attorney, Agent, or Firm—Woodard, Emhardt, Moriarty, McNett & Henry LLP

(57) ABSTRACT

The present invention relates to a formed tablet calibration standard-reagent for Karl Fischer reactions to determine the water content of substances, such as pharmaceuticals, food stuffs, and oils.

7 Claims, No Drawings

OTHER PUBLICATIONS

Burger A et al: "Polymorphism and preformulation studies of lifibrol" European Journa. of Pharmaceutics and Biopharmaceutics, Elsevier Science Publishers B.V., Amsterdam, NL, vol. 49, No. 1, Jan. 3, 2000, pp. 65-72, XP004257136 ISSN: 0939-6411 p. 66, right-hand column, paragraph 1.

* cited by examiner

CALIBRATION STANDARDS, METHODS, AND KITS FOR WATER DETERMINATION

CROSS-REFERENCE TO RELATED APPLICATIONS

This application is a continuation-in-part of U.S. patent application Ser. No. 10/399,117, filed Apr. 14, 2003, which claims priority to PCT/US01/27790, filed Nov. 1, 2001, now published as WO 02/40991, which claims priority to U.S. Provisional Patent Application No. 60/248,487, filed Nov. 14, 2000.

BACKGROUND OF THE INVENTION

This invention relates to improved calibration standard-reagents for water determination using the Karl Fischer reaction. More particularly, the invention relates to a formed tablet calibration standard-reagent for calibrating Karl Fischer reactions for determining water content in a substance. In one embodiment, the reagent contains a first component, namely sodium tartrate dihydrate, and a second component, namely magnesium stearate.

Moisture measurement is valuable because the presence of water can adversely affect a variety of applications across multiple industries. Some examples include pharmaceutical drug stability; foodstuff storage quality; properties of oils (e.g. viscosity); and reduced chemical reaction yield (e.g. production of plastics). Moisture content determination is an evaluation criterion necessary for stability considerations of New Drug Applications. Accurate control and monitoring of moisture in these fields is often required by regulatory agencies and necessary to improve product quality.

A number of chromatographic, spectroscopic, electronic, thermal, and wet chemical methods have been used in the past to determine moisture levels (S. K. MacLeod, Anal. Chem., 1991, 63, 557A–565A). The most common of these are lost on drying (LOD), thermogravimetric analysis (TGA), gas chromatography using a thermal conductivity detector, and the Karl Fischer titration. Of these most common water content measurements, however, the Karl Fischer titration has become the method of choice and is now the approach most widely used in the determination of water content. The determination of moisture in materials such as liquids and solids by the Karl Fischer reaction is well-known and widely used since it was first described by Karl Fischer in Angewandte Chemie 48, pages 394–396 (1935). Numerous publications have also described this technique for water determination, and reference is made to a general text by J. Mitchell, Jr. and D. M. Smith, entitled "Aquametry", published by John Wiley and Sons, 1980. Reference is also made to a publication by E. Scholz entitled, "Karl Fischer Titration," published by Springer Verlag in 1984.

In a Karl Fischer reaction, the water to be determined reacts with iodine on a quantitative basis and consequently, the amount of reacted iodine is a measure of the amount of water present in the sample. The reaction proceeds according to the following expression:

$$H_2O + SO_2 + I_2 = 2H^+ + 2I^- + SO_3 \quad (1)$$

The titration can be run in either protic or aprotic medium, with the protic medium seeing wider use due to higher sensitivity of the titer to sample and solvent composition (M. S. Kamat, R. A. Lodder and P. P. DeLuca, Pharmaceutical Research, 1989 6(11) 961–965). The reaction in protic media (i.e., alcohol) involves sulfur dioxide reacting with the alcohol to produce an alkyl sulfite in a buffered medium using an appropriate base to maintain the solution at the optimal pH. In a coulometric experiment, the iodine is generated electrically from iodine present in the cell. The electric efficiency of this method is generally 100%, and the amount of water in the sample is calculated from the number of moles of electrons used in the iodine generation. The components necessary to carry out this reaction have been formulated and are readily available as Karl Fischer reagents. These reagents are divided into two groups, single-component and two-component systems. In the single-component systems, all ingredients (iodine, buffer, $SO_2$, and solvent) are in one solution. In the two-component systems, the "vessel" solution contains the buffer, $SO_2$, and a solvent, while the "titrant" solution contains iodine in a suitable solvent.

Thus, Karl Fischer reagents are used in several types of analysis. A volumetric analysis using a volumetric reagent determines moisture by measuring the volume of the Karl Fischer reagent consumed during the analysis. A coulometric analysis using a coulometric reagent generates iodine by passing a current through the reagent and determines the moisture from the amount of current. The present invention can be used in the volumetric and the coulometric methods of analysis as well as the loss on drying and near infrared techniques.

Analytical instrumentation, semi-automating the Karl Fischer assay, is most commonly used to conduct Karl Fischer titrations. Working medium (Methanol) is added to the titration vessel and conditioned to equilibrium (end point with a slight excess of reagent) with titrant. The weighed sample is then delivered into the vessel for titration to the same end point. The amount of water in the sample under test is determined using the reagent strength factor (based on instrument calibration with material of known water content) and the volume of reagent dispensed to reach equilibrium.

Examples of instrumentation utilizing the Karl Fischer reaction for determination of water content comprise: 1) Volumetric Moisture Meter, Model KF-100, Mitsubishi Chemical Corporation; 2) Aquastar® Volumetric Titrator, Models VIB and V-200, EM Science; 3) Schott Titroline KF, Schott; 4) Metrohm® & Volumetric Karl Fischer Titration Systems, Models 701, 784, 758, 756, Brinkmann Instruments, Incorporated; 5) Orion® Volumetric Karl Fischer Titrators, Models TURBO2™ and AF8, Thermo Orion, Incorporated; and 6) Mettler-Toledo Titrators, Models DL53, DL55, DL58, Mettler-Toledo Corporation.

Accurate moisture content determination measurements using the Karl Fischer titration are contingent on the proper working order of the titration instrument and the chemical reactions. Successful moisture content determinations require that 1) equipment be in proper working order, 2) reagents be stable and not depleted, 3) moisture be excluded from the system, 4) the anodic reaction produce 100% current yield, 5) the cathodic reaction does not interfere with the titration, and 6) the reaction not be adversely affected by the sample matrix.

To assure that these criteria are being met, the quality of the analysis is checked against calibration standards containing known moisture content. The moisture content determination of the calibration standards confirms that the Karl Fischer titration analysis is running properly, or indicates that a problem exists. A variety of materials have been proposed as standards for moisture content determinations. The principal requirements of these materials are 1) that they contain a stoichiometric amount of moisture that is stable over a wide range of temperature and humidity, 2) solubility in the Karl Fischer titration reagents, 3) ease of handling and storage, 4) availability, and 5) uniformity (M. S. Kamat, R. A. Lodder and P. P. DeLuca, Pharmaceutical Research, 1989, 6(11), 961–965.).

Many possible calibration standards for Karl Fischer determination of water have been described. These include: purified water, certified water standards (known water content determined by assay), aluminum potassium sulfate, ammonium oxalate, citric acid, ferric ammonium sulfate, ferrous ammonium sulfate, lactose, oxalic acid, potassium citrate, potassium sodium tartrate, potassium tartrate, sodium acetate, sodium bitartrate, sodium citrate, and sulfosalicylic acid (Neuss, J. D. Obrien, and M. G. Frediani, H. A., Analytical Chemistry, 23, 1332 [1951]). Additionally, Hydranal® Standard sodium tartrate-2-hydrate, Hydranal® Standard 5.00, Hydranal® Water Standard 10.0, Hydranal® Water Standard 1.0, and Hydranal® Water Standard 0.10 may also be used.

Much effort has been given to making liquid water standard solutions less hygroscopic. These efforts have not been completely successful, as the water content of the solutions change after the septum over the solutions has been pierced several times. Water is a very good calibration reagent, but it is difficult to accurately dispense liquid water into the Karl Fischer titrator. When delivered by volume, the inaccuracies of the small amount delivered make it difficult to obtain an accurate value. A more accurate measurement is obtained when the liquid water is delivered by weight, but this again presents difficulties in dispensing the water into the titrator. Also, degradation and stability of the standard become relevant due to the special material handling characteristics that must be considered for certified liquid calibration media.

Use of sodium tartrate dihydrate in powder form as a calibration standard for KF reactions is known in the art (E. Scholz, Karl Fischer Titration-Determination of Water-Chemical Laboratory Practice, Springer-Verlag, N.Y. 1984, T. H. Beasley, H. W. Siegler, R. L. Charles and P. King, Anal. Chem., 1972, 44, 1833–1840). However, bulk powder calibration standards are difficult to manipulate, which can result in increased assay variability due to the ingress of ambient moisture and the residual standard unaccounted for during sample addition. Another problem with the sample transfer process of the prior art is dispensing the calibration standard material into the Karl Fischer titrator. When trying to pour the powder material through a funnel into the titrator, some material is lost into the atmosphere or adheres to the sampling funnel, and thus is not all dispensed into the titrator. To mitigate this detriment, weighing paper can be rolled to create a funnel, but this requires operator dexterity. In either case, during the transfer of the powder, the titrator is open to the atmosphere, and the length of time the vessel is open is inversely related to the accuracy of the determination. Therefore, the prior art method using powder calibration standards requires significant analyst time and creates variability in assay results.

Thus, in its prior art configuration, Karl Fischer titrations were affected by: 1) sample transfer time, 2) relative humidity in the laboratory, and 3) material lost in the material transfer. These factors make it desirable to have an improved calibration standard reagent. Such an improved reagent would result in reduced time to load the reagent, provide for more accurate and quantitative transfer, and have less fluctuation in water content, as compared to the prior art liquid and powder calibration standards.

Accordingly, it is an object of this invention to provide a formed tablet calibration standard-reagent for calibrating Karl Fischer reactions for determining water content in a substance. It is another object of this invention to provide an improved process for the determination of water in a sample using the Karl Fischer reaction, in which the calibration standard-reagent that is employed is a formed tablet calibration standard-reagent. In one embodiment, the formed tablet calibration standard-reagent contains a first component, namely sodium tartrate dihydrate, and a second component, namely magnesium stearate.

The formed tablet calibration standard-reagent may include only the active component (such as sodium tartrate dihydrate), or may include the active component and any number of other components such as excipients. Excipients are used in the art of tablet making to improve the qualities of the formed tablet, improve the efficiency of the tablet making process, and improve the efficacy and/or bioavailability of the tablet when used. Some typical excipients include fillers, binding agents, disintegrants, super disintegrates, glidants, lubricants, dyes, and film and aqueous coatings. Fillers and binding agents can be used to raise the total tablet weight to a desired target weight for content uniformity and provide adhesiveness to hold the tablet together. Disintegrants and super disintegrants promote the break up of the tablet upon use. Glidant improves the flowability within the tablet making equipment, such a press. Lubricant inhibits sticking or binding of the bulk tablet mixture with the tablet making tooling. Dyes are used to add color to aid in product identification. Film and aqueous coatings are used to protect the active and other components and can be used to control the release of the active component upon use of the tablet.

Excipients are selected based upon the specific physical or chemical properties they provide. Many other excipients can be used in the tablet making process. Some common fillers include lactose, starch, dibasic calcium phosphate, microcrystalline cellulose (MCC), calcium carbonate, sucrose, mannitol, sorbital, acidisol, alcohol, calcium sulfate, dextrose, and dicalcium phosphate dehydrate (Ditab). Some common binding agents include acacia gum, gelatin, sucrose, povidone, methylcellulose, carboxymethylcellulose, hydrolyzed starch pastes, and MCC. Some common disintegrating agents include starch, chemically modified starches and cellulose, alginic acid, MCC, cross-linked povidone, effervescent mixtures, apple pectin, avicel, croscarmellose sodium, and sodium starch glycolate. Some common lubricants include magnesium stearate, metallic stearates, stearic acid, hydrogenated vegetable oils, talc, polyethylene glycols, lauryl sulfate salts, and calcium stearate. Some common dyes include D and C dye, FD and C dyes and lakes. Some common aqueous coatings include sugar with insoluble starch/$CaCO_3$/talc/titanium dioxide suspended in acacia/gelatin. Some common film coatings include hydroxypropyl methylcellulose, methyl cellulose, hydroxypropylcellulose, carboxymethylcellulose sodium, and mixtures of cellulose acetate phthalate and polyethylene glycols.

In addition to formed tablets, other means of delivery of the active component may be used. For example, the active component could be included in bodies such as gelcaps, geltabs, capsules, caplets, containers, pills, lozenges, enclosed vessels, or foil pouches containing the active component in either liquid or solid (i.e., a powder) form. In one example, a measured amount of sodium tartrate dihydrate powder or water is included in any of the above-described bodies (or equivalents) that are configured to dissolve in the Karl Fischer reagent.

A formed tablet calibration standard-reagent would fundamentally reduce variability in the Karl Fischer assay. Differences due to analyst technique would be minimized because standard addition is simplified and more consistent. Cumbersome use of a syringe and injection into the titration vessel would be replaced with a single hand transfer of the tablet to the vessel through the sample port. Titration methodology would remain the same in all other aspects with the exception of instrument calibration. A formed tablet calibration standard would improve upon the prior art which acts to deter the automation of Karl Fischer determination of water content. An automated Karl Fischer assay employing a formed tablet calibration standard would increase productivity in Karl Fischer water determinations.

These and other objects, features, and advantages will be apparent from the following more particular description of the preferred embodiments of the invention.

SUMMARY OF THE INVENTION

The invention relates to a formed tablet calibration standard-reagent for calibrating Karl Fischer reactions for determining water content in a substance. In one embodiment, the formed tablet includes at least one of the possible calibration standards for Karl Fischer reactions selected from the group of aluminum potassium sulfate, ammonium oxalate, citric acid, ferric ammonium sulfate, ferrous ammonium sulfate, lactose, oxalic acid, potassium citrate, potassium sodium tartrate, potassium tartrate, sodium acetate, sodium bitartrate, sodium citrate, sulfosalicylic acid, or any composition suitable for Karl Fischer reactions and an excipient. In another embodiment the reagent contains a first component, namely sodium tartrate dihydrate, and a second component, namely magnesium stearate, where the ratio by percent weight of said first component to a second component is from 99.7:0.3 to 99:1.

The invention further relates to a method for determining the water content of a substance using a Karl Fischer analysis wherein, the reaction is calibrated using a calibration standard, the improvement comprising using said formed tablet calibration standard-reagent. The invention further relates to a formed tablet calibration standard-reagent kit, comprising a sealed package containing said formed tablet calibration standard-reagent.

DETAILED DESCRIPTION OF THE INVENTION

As used herein, "Karl Fischer reaction" refers to the chemical reaction described by equation (1) supra, and all of the embodiments of that reaction herein described including those that employ semi-automated instrumentation (described supra).

While, throughout this description, tablets are described as the vehicle for delivering a calibration standard, it should be understood that formed tablets are just one example of a delivery vehicle. In other embodiments of the invention, delivery vehicles such as gelcaps, geltabs, capsules, caplets, containers, pills, lozenges, enclosed vessels, or foil pouches containing the active component in either liquid or solid (i.e., a powder) form are used. In these embodiments, a measured amount pursuant to equations 2 and 3 is either incorporated into or enclosed within the selected delivery vehicle. The tablets described herein for use in calibrating Karl Fischer reactions may be formed by the customary procedures in the art of tablet making. In one embodiment of the present invention, it is preferable that a ratio of a first component to a second component is from 99.7:0.3 to 99:1. Preferably, the ratio is between 99.6:0.4 and 99.4:0.6. Most preferably, the ratio is 99.5:0.5. The tablet may have a total weight ranging from about 25 milligrams to 500 milligrams. Preferably, the total weight is from about 50 milligrams to 500 milligrams. In one embodiment, most preferably the total weight is about 200 milligrams.

In one embodiment of the present invention, of all the possible calibration standard materials described above, sodium tartrate dihydrate was selected for preparation of the formed tablet calibration standard-reagent. Bulk sodium tartrate is nearly 100% pure and stable for an extended duration, without special storage requirements. In addition, sodium tartrate has a known theoretical moisture content. These advantages are incorporated into the tablet because of the formulation process. In one embodiment of the present invention, after size exclusion of larger crystals, the tartrate is compressed to form a tablet of the desired weight having a target water content. For example, 2 mg, 10 mg, 25 mg, and 30 mg, are common amounts of water for which tablets can be made, but a tablet can be formulated to include the appropriate amount of the active component to result in any desired amount of water.

The weight of the active component of the tablet determines its water content. For example, if a 200 mg tablet is desired with 10 mg of water for a calibration test, using sodium tartrate dihydrate, the calculation for determining the content of the tablet is as follows:

Sodium tartrate dihydrate: $C_4H_4Na_2O_6 \cdot 2H_2O$ $$\frac{\text{Stoichiometric weight of water in sodium tartrate dihydrate}}{\text{Stoichiometric weight of sodium tartrate dihydrate}} = \frac{2*18.02}{230.08} = 0.1566 \quad (2)$$

In other words, water is 15.6% of the stoichiometric weight of sodium tartrate dihydrate. The following equation is used to determine how much sodium tartrate dihydrate is required to yield 10 mg of water:

$$\frac{10 \text{ mg } H_2O}{\text{tablet}} \cdot \frac{1 \text{ mg } C_4H_4Na_2O_6 \cdot 2H_2O}{0.1556 \text{ mg } H_2O} = \frac{64 \text{ mg } C_4H_4Na_2O_6 \cdot 2H_2O}{\text{tablet}} \quad (3)$$

Based on equation 3, approximately 64 mg of sodium tartrate dihydrate is required to yield approximately 10 mg of water. The balance of the 200 mg tablet may be excipients such as filler, binding agents, glidants, and lubricants. These calculations can be used to determine the amount of active component required for any suitable Karl Fischer calibration standard such as those listed above.

The target amount of water in the tablet is determined based on the optimum operating range of the titrator being used. When the water content of the replicate under test falls within this range, the variability in the assay is reduced. Since operating ranges vary by manufacturer, range appropriate sized tablets can be developed for optimal results in a specific instrument type. Any size tablet with any target quantity of water can be made with any suitable Karl Fischer calibration standard.

The addition of magnesium stearate improved tablet robustness and eliminated capping. The quantity and characteristics of the excipients added to tablets is generally based upon the total tablet weight. For example, the amount of disintegrants used in a tablet may be about 10–20% of the total tablet weight while a super disintegrant may be only 2–5% of the total tablet weight. Glidants and lubricants generally make up about 0.5–1.0% of the total tablet weight. However, the excipients used and their respective quantities vary for different compositions and are generally determined experimentally.

In the present invention, the development of the tablet formulation included experimentation to assess compression and tablet hardness versus release of moisture in the Karl Fischer assay. In one embodiment, tablets were formulated with 0.25% magnesium stearate (based on the weight of the sodium tartrate dihydrate); however, tablet production failed. The lack of sufficient lubricant caused the press to seize during production. Another embodiment was used for tablet production with. 0.5% magnesium stearate based on the weight of the sodium tartrate dihydrate. In yet another embodiment, a 100 mg tablet was made with 0.5% (based on the total tablet weight) or 0.5 mg of lubricant (magnesium stearate) which produced a properly formed tablet without any production problems. This will be explained in more detail by reference to the following examples, which are merely illustrative, and not limiting of the invention.

EXAMPLE 1

Sodium tartrate dihydrate, ACS reagent grade, was used as the starting material to make formed tablets. Crystals were sieved through a #30 mesh screen (Fischer Standard Testing Sieve, 600 micrometer opening), and placed in a common container. Retained material was discarded. To promote formation of the tablet, magnesium stearate was added to the filtered crystals by sizing through the same screen, and adding the excipient to the mixture. The two components, sodium tartrate and magnesium stearate, were mixed at a ratio of 99.5:0.5 percent by weight for 30 minutes using a "tumble" style mixing apparatus to achieve homogeneity.

The homogeneous mixture was then compressed into formed tablets using a common tablet press. A 7-millimeter round tool and die set was selected to form the tablets. Tablet production was carried out according to customary practices in the art. The tablets produced by this procedure were found to have an average thickness of 0.155–0.160 inches, and an average hardness of 1.3 KP.

The resulting tablets were surprisingly well formed and durable. In previous attempts to form tablets without magnesium stearate, or with 0.25% magnesium stearate, the tablets were not well formed and could not be handled without degradation of the tablets. The hardness of the tablet is known in the art of tablet making to be important to the structural and functional characteristics of the tablet. Further, it is known in the art of tablet making that generally the greater the force that is applied to the materials to be formed, the greater the hardness of the resulting tablet. Surprisingly, it was discovered that formation of the tablets of the present invention did not follow this relationship. Unexpectedly it was determined that the combination of sodium tartrate dihydrate with magnesium stearate in the ratio of 99.5:0.5 produced tablets of optimal hardness. Tablets formed of this ratio were subsequently determined in Karl Fischer water determination analysis to provide results that were closest to the theoretical water content of sodium tartrate dihydrate, and therefore are most preferable as a formed tablet calibration standard-reagent.

Surprisingly, the tablets formed with 0.5% magnesium stearate could be handled and used in the methods of Karl Fischer water determination described herein without crumbling and without the losses of material to the environment or upon contact with transferring instruments such forceps or weighing boats. The compact and discrete nature of the tablets minimized the handling requirements by the analyst, which resulted in less time to execute the analysis. The formed tablet calibration standard reagent was superior to the use of powder or liquid standard reagents in that analyst time was not required to aliquot the standard, and in that the transfer process was discrete and expedient.

EXAMPLE 2

In another embodiment of the present invention, tablets were formed with approximately 38.5 mg of filler, 64 mg of active ingredient, and 0.5 mg of lubricant to produce a tablet having a target weight of approximately 100 mg. The tablet produced had good tablet qualities and no problems were experienced during tablet production.

Several experiments have been conducted to show that the formed tablet calibration standard-reagent of the present invention would produce values in Karl Fischer water determinations consistent with the expected theoretical value for sodium tartrate dihydrate. Consistency with the expected value is necessary in order for the tablet to be useful as a calibration standard reagent for Karl Fischer water determinations.

The formed tablet calibration standard-reagents prepared with 99.5% sodium tartrate dihydrate and 0.5% magnesium stearate were analyzed by Karl Fischer analysis. A commercial titration apparatus was used for the assays (Orion® Volumetric Karl Fischer Titrators, Models TURBO2™). Each moisture analysis was conducted according to the customary procedures for this instrument. Briefly, the instrument is standardized by accurately weighing by difference approximately 30 mg of a liquid standard, namely Hydranal® water standard 10.0. The aliquot was delivered into the titration vessel and titrated to the end point with Karl Fischer reagent according to customary procedures. The tablets of Example 1 were then analyzed and water content was determined by customary procedure for this instrument. The empirical values observed were within 5 percent of the theoretical water content calculated for the sodium tartrate dihydrate tablets.

A preferred embodiment of the present invention pertains to the use of the formed tablet calibration standard-reagent for calibrating Karl Fischer wherein the Karl Fischer reaction employs the two-component reagent system described supra. Surprisingly, it was determined that the two-component system has a greater capacity for repeated analyses as compared to the one component system when using the formed tablet calibration standard-reagent.

The invention further relates to a method for determining the water content of a substance using a Karl Fischer analysis, wherein the reaction is calibrated using a calibration standard, the improvement comprising using a formed tablet calibration standard-reagent.

The formed tablet calibration standard-reagent is used to calibrate the Karl Fischer reaction for determining water content in test substances. In use, the formed tablet calibration standard-reagent replaces the prior art calibration standard in the method of calibrating the Karl Fischer reaction and determining the water content of test samples. As described above, the tablet can be made to any desired weight and contain any amount of water needed for a calibration test. Use of the tablet provides several advantages over the prior art standards, including reducing the time and effort required of the analyst and reducing the time the reaction vessel is open to the environment. Further, a formed tablet calibration standard-reagent improves upon liquid and bulk-powder standards to complete automation of the assay. Material handling of samples in tablet form is easily manipulated by robotics. The formed tablet calibration standard-reagent simplifies the requirements for assay automation, and is particularly well suited for pharmaceutical applications where the samples for water content determination are often pills or tablets. This simplified automation strategy would replace repetitious, tedious, and variable manual determinations of moisture content.

The invention further relates to a formed tablet calibration standard-reagent kit, comprising a sealed package containing a formed tablet calibration standard-reagent. These new reagents can be employed in kits that are sold to users for the determination of water content. An example is a sealed package containing these new reagents, where the calibration tablet can be easily removed from the sealed package and introduced into the Karl-Fischer reaction vessel.

While the invention has been described with respect to particular embodiments thereof, it will be apparent to those of skill in the art that variations can be made therein without departing from the spirit and scope of the invention. The intended scope of the invention is to be limited only by the issued claims thereof.

The invention claimed is:

1. A method for calibrating a Karl Fischer reaction for determining water content of a test substance, comprising conducting a calibrating Karl Fischer reaction with a calibration standard-reagent,
   said calibration standard-reagent comprising a discrete body configured as a calibration standard-reagent for a Karl Fischer reaction, said discrete body formed by compression of a material including at least one water-containing ingredient effective to interact with a Karl Fischer reagent, said discrete body including a known target amount of water and configured for delivery in its entirety into the Karl Fischer reagent; and
   said conducting including a step of combining the calibration standard-reagent with a Karl-Fischer reagent.

2. The method of claim 1, wherein the discrete body comprises a lubricant.

3. The method of claim 2, wherein the lubricant is magnesium stearate.

4. The method of claim 3, wherein the discrete body also comprises a disintegrating agent.

5. The method of claim 4, wherein the disintegrating agent is a starch, chemically modified starch, or sodium starch glycolate.

6. The method of claim 5, wherein the discrete body also comprises at least one of a chemically modified cellulose and microcrystalline cellulose.

7. The method of claim 6, wherein the discrete body also comprises microcrystalline cellulose.

* * * * *